United States Patent [19]

Marshall et al.

[11] 4,226,887
[45] Oct. 7, 1980

[54] ANTI-INFLAMMATORY AGENTS

[75] Inventors: Winston S. Marshall, Bargersville; William Pfeifer, Indianapolis, both of Ind.

[73] Assignee: Eli Lilly and Company, Indianapolis, Ind.

[21] Appl. No.: 29,970

[22] Filed: Apr. 16, 1979

Related U.S. Application Data

[62] Division of Ser. No. 522,006, Nov. 8, 1974, which is a division of Ser. No. 428,163, Dec. 26, 1973, Pat. No. 3,991,212.

[51] Int. Cl.$^3$ .......................................... A61K 31/015
[52] U.S. Cl. ............................................. 424/356
[58] Field of Search ........................................ 424/356

[56] References Cited

U.S. PATENT DOCUMENTS 3,852,364  12/1974  Diamond ........................ 260/649 R

FOREIGN PATENT DOCUMENTS 2334425  3/1972  Fed. Rep. of Germany .
2190462  3/1972  France .

*Primary Examiner*—Stanley J. Friedman
*Attorney, Agent, or Firm*—Kathleen R. S. Page; Everet F. Smith

[57] ABSTRACT

This invention is directed to the use of certain arylacetylene compounds, principally as anti-inflammatory agents but also as anti-pyretic agents and as analgesic agents.

3 Claims, No Drawings

ANTI-INFLAMMATORY AGENTS

This is a division of application Ser. No. 522,006, filed Nov. 8, 1974, which is a division of application Ser. No. 428,163, filed Dec. 26, 1973, issued Nov. 9, 1976 as U.S. Pat. No. 3,991,212.

BRIEF SUMMARY OF THE INVENTION

The present invention is directed to methods employing, and compositions comprising, arylacetylene compounds of the following formula:

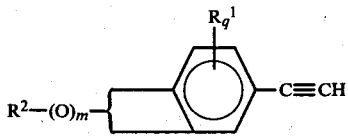

wherein q represents 0, 1, or 2; each $R^1$ independently represents chloro, fluoro, methyl, or methoxy; m represents 0 or 1; and $R^2$ represents
(1) phenyl;
(2) substituted phenyl of the formula

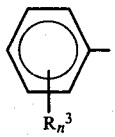

wherein each $R^3$ independently represents chloro, fluoro, or methyl, and n represents 1 or 2; or
(3) where q=1 and at least one $R^1$=chloro, fluoro, or methyl,
 (a) n-butyl or
 (b) cycloalkyl of $C_5$-$C_7$.

The bracket unit "{" is employed to indicate that the $R^2$—$(O)_m$—substituent is attached to the phenyl ring at a position either meta or para to the acetylene moiety.

The above described compounds exhibit anti-inflammatory activity, as well as analgesic activity and antipyretic activity. Certain of the compounds are novel and are claimed per se.

DETAILED DESCRIPTION OF THE INVENTION

The compounds to be employed in accordance with the present invention are prepared by any of several synthetic routes. The most preferred route is as follows

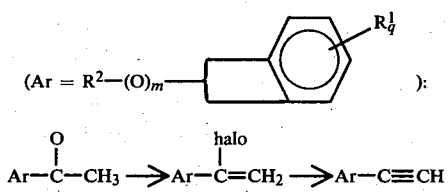

In this route, an acetophenone is halogenated, typically brominated or chlorinated, to obtain an α-halostyrene, which on dehydrohalogenation yields the desired compound. Although halogenation of a carbonyl compound is generally carried out with phosphorous pentabromide or pentachloride, equivalent results have been obtained in the present synthesis by using a mixture of the phosphorous pentahalide with the corresponding phosphorous oxyhalide. The amounts of these agents are not critical; conveniently, an excess is employed, the phosphorous oxyhalide serving as a reaction medium. However, other inert reaction media, such as benzene, toluene, etc., can be used. The reaction goes best at elevated temperatures, such as 40°-200° C. Separation and, if desired, purification, are carried out in conventional procedures.

In the second step of this reaction route, the resulting α-halostyrene is dehydrohalogenated. The identity of reagent is not critical; strong bases such as sodium amide, lithium amide, or potassium amide in solution in liquid ammonia, or potassium tertiary butoxide in dimethyl sulfoxide, give good results. The dehydrohalogenation is preferably conducted at temperatures of −30° to 0° C. Separation and purification, if desired, are carried out in conventional procedures.

In an alternate synthetic route, an arylstyrene is halogenated (Br, Cl, or I) and subsequently dehydrohalogenated:

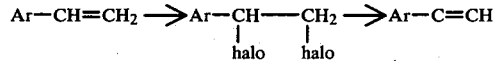

The halogenation reaction is generally run at low temperatures, such as −20° to 20° C., using as reaction medium an inert organic solvent such as chloroform, methylene chloride, diethyl ether, benzene, or toluene. Separation and purification are carried out in conventional procedures.

The subsequent dehydrohalogenation reaction is carried out as discussed above in the first synthetic route.

The following examples illustrate the synthesis of the compounds to be employed in the present invention.

EXAMPLE 1

(4-(2-FLUOROPHENYL)PHENYL)ACETYLENE

A mixture of 86.5 g. of 4'-(2-fluorophenyl)acetophenone, 94 g. of phosphorus pentachloride, and 225 ml. of phosphorus oxychloride was heated at 60° C. for 20 hours. After cooling, the mixture was evaporated in vacuo and the residue, containing 4-(2-fluorophenyl)-α-chlorostyrene, was azeotroped four times with dry benzene. The residue was dissolved in tetrahydrofuran and added dropwise to a solution of sodium amide prepared by addition of 46 g. of metallic sodium to 1500 ml. of liquid ammonia containing a few mg. of ferric chloride. After 750 ml. of dry diethyl ether were added, the reaction was stirred overnight. The reaction was treated with 150 ml. of saturated ammonium chloride solution, then with 100 ml. water and poured onto ice. The organic layer was separated and the aqueous layer was extracted with diethyl ether and ethyl acetate. The combined organic extracts were washed with water, 5% hydrochloric acid, and water, and dried over sodium sulfate. Evaporation of the solvents in vacuo left a liquid residue which was fractionally distilled to yield 30.7 g. of (4-(2-fluorophenyl)phenyl)acetylene, b.p. 94°-97° C./0.2 mm., $n_D^{24}$=1.6185. On standing, the compound solidified, m.p. 28.5°-31.0° C.

Analysis, Calc. for $C_{14}H_9F$: C, 85.69; H, 4.62; F, 9.68. Found: C, 85.46; H, 4.45; F, 9.39.

EXAMPLES 2-24

The following compounds were prepared from the indicated ketone according to the method of Example 1, using appropriate amounts of phosphorus pentachloride, phosphorus oxychloride, sodium amide, and ammonia:

4-Biphenylylacetylene, m.p. 76°-81° C., from 4'-phenylacetophenone.

Analysis, Calc. for $C_{14}H_{10}$: C, 94.34; H, 5.66. Found: C, 94.16; H, 5.87.

(2-Methyl-4-phenoxyphenyl)acetylene, b.p. 110°-112° C./0.35 mm., $n_D^{25}$=1.5994, from 2'-methyl-4'-phenoxyacetophenone.

Analysis, Calc. for $C_{15}H_{12}O$: C, 86.51; H, 5.81; O, 7.68. Found: C, 86.24; H, 6.02; O, 7.63.

(3-Methyl-4-phenoxyphenyl)acetylene, b.p. 103°-105° C./0.1 mm., $n_D^{23}$=1.5949, from 3'-methyl-4'-phenoxyacetophenone.

Analysis, Calc. for $C_{15}H_{12}O$: C, 86.51; H, 5.81; O, 7.68; Found: C, 86.42; H, 5.81; O, 7.39.

(4-Phenoxyphenyl)acetylene, b.p. 105°-111° C./0.3 mm., $n_D^{25}$=1.6045, from 4'-phenoxyacetophenone.

Analysis, Calc. for $C_{14}H_{10}O$=C, 86.57; H, 5.19; O, 8.24. Found: C, 86.31; H, 4.97; O, 8.24.

(3-Methoxy-4-phenylphenyl)acetylene, b.p. 133°-134° C./0.2 mm., from 3'-methoxy-4'-phenylacetophenone.

Analysis, Calc. for $C_{15}H_{12}O$: C, 86.51; H, 5.81. Found: C, 86.26; H, 5.94.

(3-Phenoxyphenyl)acetylene, b.p. 90° C./0.2 mm., $n_D^{23}$=1.5987, from 3'-phenoxyacetophenone.

Analysis, Calc. for $C_{14}H_{10}O$: C, 86.57; H, 5.19; O, 8.24. Found: C, 86.30; H, 5.18; O, 8.04.

(3,5-Dimethyl-4-phenoxyphenyl)acetylene, b.p. 145°-146° C./0.1 mm., $n_D^{25}$=1.5882, from 3',5'-dimethyl-4'-phenoxyacetophenone.

Analysis, Calc. for $C_{16}H_{14}O$: C, 86.45; H, 6.35; O, 7.20. Found: C, 86.20; H, 6.37; O, 7.17.

3-Biphenylylacetylene, b.p. 98°-100° C./0.4 mm., $n_D^{25}$=1.6300, from 3'-phenylacetophenone.

Analysis, Calc. for $C_{14}H_{10}$: C, 94.34; H, 5.66. Found: C, 94.53; H, 5.43.

(3-Chloro-4-cyclohexylphenyl)acetylene, b.p. 108°-112° C./0.4 mm., $n_D^{25}$=1.5698, from 3'-chloro-4'-cyclohexylacetophenone.

Analysis, Calc. for $C_{14}H_{15}Cl$: C, 76.88; H, 6.91. Found: C, 76.73; H, 6.84.

(4-(2-Chlorophenyl)phenyl)acetylene, b.p. 101°-106° C./0.1 mm., from 4'-(2-chlorophenyl)acetophenone.

Analysis, Calc. for $C_{14}H_9Cl$: C, 79.06; H, 4.27; Cl, 16.67. Found: C, 78.92; H, 4.55; Cl, 16.41.

(2-Methoxy-4-phenylphenyl)acetylene, m.p. 53°-55° C., from 2'-methoxy-4'-phenylacetophenone.

Analysis, Calc. for $C_{15}H_{12}O$: C, 86.51; H, 5.81; O, 7.68. Found: C, 86.43; H, 6.07; O, 7.48.

(4-(3-Fluorophenyl)phenyl)acetylene, b.p. 87°-89° C./0.07 mm., $n_D^{25}$=1.6229, from 4'-(3-fluorophenyl)acetophenone.

Analysis, Calc. for $C_{14}H_9F$: C, 85.69; H, 4.62; F, 9.68. Found: C, 85.48; H, 4.87; F, 9.40.

(4-(2,4-Difluorophenyl)phenyl)acetylene, b.p. 95°-101° C./0.1 mm., from 4'-(2,4-difluorophenyl)acetophenone.

Analysis, Calc. for $C_{14}H_8F_2$: C, 78.50; H, 3.76. Found: C, 78.48; H, 4.01.

(4-(2,5-Difluorophenyl)phenyl)acetylene, b.p. 100°-102° C./0.2 mm., from 4'-(2,5-difluorophenyl)acetophenone.

Analysis, Calc. for $C_{14}H_8F_2$: C, 78.50; H, 3.76. Found: C, 78.71; H, 4.03.

(2-Methyl-4-n-butoxyphenyl)acetylene, b.p. 100° C./0.4 mm., from 4'-n-butoxy-2'-methylacetophenone.

Analysis, Calc. for $C_{13}H_{16}O$: C, 82.94; H, 8.57; O, 8.50. Found: C, 83.22; H, 8.70; O, 8.31.

(4-(2,6-Difluorophenyl)phenyl)acetylene, m.p. 81°-83° C., from 4'-(2,6-difluorophenyl)acetophenone.

Analysis, Calc. for $C_{14}H_8F_2$: C, 78.50; H, 3.76; F, 17.74. Found: C, 78.27; H, 3.99; F, 17.98.

(4-(o-Tolyl)phenyl)acetylene, m.p. 29°-30° C., from 4'-(o-tolyl)acetophenone.

Analysis, Calc. for $C_{15}H_{12}$: C, 93.71; H, 6.29. Found: C, 93.50; H, 6.38.

(3-Methyl-4-phenylphenyl)acetylene, m.p. 57°-59° C., from 3'-methyl-4'-phenylacetophenone.

Analysis, Calc. for $C_{15}H_{12}$: C, 93.71; H, 6.29. Found: C, 91.63; H, 6.24.

(3-Chloro-4-phenylphenyl)acetylene, b.p. 97°-100° C./0.09 mm., from 3'-chloro-4'-phenylacetophenone.

Analysis, Calc. for $C_{14}H_9Cl$: C, 79.06; H, 4.27. Found: C, 78.81; H, 4.07.

(3-Fluoro-4-phenylphenyl)acetylene, b.p. 103° C./0.6 mm., from 3'-fluoro-4'-phenylacetophenone.

Analysis, Calc. for $C_{14}H_9F$: C, 85.69; H, 4.62; F, 9.68. Found: C, 85.48; H, 4.66; F, 9.42.

(4-Fluoro-3-(2-fluorophenyl)phenyl)acetylene, b.p. 112°-120° C./0.05 mm., from 4'-fluoro-3'-(2-fluorophenyl)acetophenone.

Analysis, Calc. for $C_{14}H_8F_2$: C, 78.50; H, 3.76; F, 17.74. Found: C, 77.0; H, 3.84; F, 17.66.

(4-(2-Fluorophenoxy)phenyl)acetylene, b.p. 110°-114° C./0.3 mm., $n_D^{25}$=1.5860, from 4'-(2-fluorophenoxy)acetophenone.

Analysis, Calc. for $C_{14}H_9FO$: C, 79.23; H, 4.27. Found: C, 79.00; H, 4.41.

(3-(2-Fluorophenoxy)phenyl)acetylene, b.p. 93°-96° C./0.2 mm., from 3'-(2-fluorophenoxy)acetophenone.

Analysis, Calc. for $C_{14}H_9FO$: C, 79.23; H, 4.27; F, 8.95. Found: C, 78.95; H, 4.30; F, 8.71.

EXAMPLE 25

4-BIPHENYLYLACETYLENE

A solution of 19.2 g. of bromine in carbon tetrachloride was added dropwise to a cooled, stirred carbon tetrachloride solution of 21.3 g. of 4-phenylstyrene. Cooling was maintained during the bromine addition so that the reaction temperature did not exceed 5° C. The reaction mixture was allowed to warm to room temperature and was then stirred overnight and poured into ice water. The carbon tetrachloride layer was separated and the aqueous layer was extracted with additional carbon tetrachloride. The combined carbon tetrachloride solutions were washed with water, dried over sodium sulfate, and evaporated to dryness in vacuo to yield crude 4-(1,2-dibromoethyl)biphenyl, m.p., 123°-126° C.

Analysis, Calc. for $C_{14}H_{12}Br_2$: C, 49.45; H, 3.56; Br, 46.99. Found: C, 49.34; H, 3.73; Br, 47.07.

A solution of 39 g. of the 4-(1,2-dibromoethyl)biphenyl in 400 ml. of a 1:1 mixture (by volume) of dimethyl sulfoxide and tert-butanol was added rapidly, with cooling (10°-15° C.) and stirring to a solution of 26 g. of potassium-tert-butoxide in 400 ml. of a 1:1 mixture (by volume) of dimethyl sulfoxide and tert-butanol. After stirring for 20 minutes, the reaction mixture was poured into ice water. The aqueous mixture was extracted with diethyl ether. The ether extract was washed with water, 5% sodium bicarbonate, and water, and dried over sodium sulfate. The ether was evaporated in vacuo, and the residue crystallized from ethanol and water to yield 18.5 g. of crude 4-biphenylylacetylene, m.p. 79°–81° C. Two recrystallizations from hexane gave pure 4-biphenylylacetylene, m.p. 82°–85° C.

Analysis, Calc. for $C_{14}H_{10}$: C, 94.34; H, 5.66. Found: C, 94.27; H, 5.68.

Preferred compounds are those wherein m=O and $R^2$=phenyl, substituted phenyl as defined or cycloalkyl as defined and the $R^2$ group is at the para position. Yet more preferred compounds are those of the last-described group bearing one substituent ortho to the phenyl-phenyl or cycloalkyl-phenyl bond. Preferred specific compounds are 4-biphenylylacetylene; (4-(2-fluorophenyl)phenyl)acetylene; (4-(2,5-difluorophenyl)phenyl) acetylene; 4-(2,4-difluorophenyl) phenyl)acetylene; (4-(2-chlorophenyl)phenyl)acetylene; (3-chloro-4-cyclohexylphenyl)acetylene; (4-(o-tolyl)-phenyl)acetylene; (3-chloro-4-phenylphenyl)acetylene; (3-fluoro-4-phenylphenyl)acetylene; and (3-methyl-4-phenylphenyl)acetylene. Compounds which are claimed as compounds are (4-(2-fluorophenyl) phenyl)acetylene; (3-chloro-4-phenylphenyl)acetylene; (3-methyl-4-phenylphenyl)acetylene; (3-fluoro-4-phenylphenyl) acetylene; (4-(2,4-difluorophenyl)phenyl)acetylene; and (4-(2,5-difluorophenyl)phenyl)acetylene.

As set forth above, the compounds to be employed in accordance with the present invention exhibit anti-inflammatory, analgesic, and antipyretic activity. The present invention is therefore directed to methods employing the compounds for the treatment of inflammation, fever, and pain. In the practice of these methods, one or more of the compounds is administered to a warm blooded animal needing such treatment, thereby alleviating symptoms of inflammation, fever, and pain. The circumstances causing these various symptoms are legion. The compounds to be employed in accordance with the present invention are especially suited to be used in the management of rheumatoid arthritis. However, those skilled in the art will recognize that the present methods will also be effective in the treatment of numerous other conditions which produce inflammation, fever, or pain, such as rheumatoid spondylitis, degenerative joint disease, and minor conditions of inflammation, pain, or fever of unspecified origin.

The amount of the compound or compounds employed is not critical, as long as an effective, anti-inflammatory, anti-pyretic, or analgesic amount is used. In general, anti-inflammatory activity is exhibited at doses of from 0.01 to 50 or more mg./kg. of animal body weight. Anti-pyretic activity is typically exhibited at doses of from 10 to 100 mg./kg. of animal body weight, while analgesic activity is generally exhibited at doses of from 1 to 100 mg./kg. of animal body weight. The dose may be repeated where continued thereapy is appropriate.

In carrying out the methods of the present invention, it is generally preferred to employ a composition comprising the active agent and one or more adjuvants suited to the particular route of administration. Compositions for oral administration may be either solid, e.g., capsules, tablets, pills, powders, etc., or liquid, e.g., emulsions, solutions, suspensions, syrups, elixirs, etc.

Inasmuch as some of the compounds to be employed as active agent are liquids, soft elastic gelatin capsules are often suitably employed for oral administration. In any of these various forms, the active agent can be combined with conventional adjuvants. In the case of solid formulations, suitable adjuvants include inert substances such as sucrose, lactose, and starch. In the case of liquid formulations, suitable adjuvants include water, mineral oil, etc. Either solid or liquid formulation can include lubricating agents, wetting agents, emulsifying and suspending agents, preserving agents, sweetening agents, flavoring agents, or perfuming agents.

In the instance of rectal administration, the compounds are suitably formulated as a suppository, such as by combination with an excipient such as cocoa butter. A hardening agent may appropriately be added to adjust the melting point of the suppository.

In the instance of parenteral administration, the compounds of the present invention are formulated in a suitable sterile, injectable liquid.

Formulations suitable for topical administration include lotions, ointments, creams, sprays, etc. Conventional adjuvants are employed.

In general, oral administration is preferred. Accordingly, a preferred formulation is a pharmaceutical preparation in dosage unit form adapted for administration to obtain an anti-inflammatory, antipyretic, or analgesic effect, composing, per dosage unit, an effective nontoxic amount within the range from about 1 to about 1000 milligrams of one or more of the compounds to be employed in accordance with the present invention. In many applications, the above preparation may suitably contain only a lesser amount of active agent, such as from about 5 to about 500 milligrams, or an even lesser amount of active agent, such as from about 25 to about 135 milligrams.

The following examples illustrate the methods and formulations of the present invention.

EXAMPLE 26

(4-(2-Fluorophenyl)phenyl)acetylene is added to microcrystalline cellulose in amounts representing 20 percent of the former and 80 percent of the latter (by weight), and the substances are then mixed by any suitable means, such as by grinding with a mortar and pestle. The formula may be encapsulated in a size of hard gelatin capsule suitable to contain the desired dose.

In a specific preparation, 540 mg. of a 20 percent formulation of (4-(2-fluorophenyl)phenyl)acetylene on microcrystalline cellulose was filled into a gelatin capsule, size 00. Each such capsule contained approximately 108 mg. of (4-(2-fluorophenyl)phenyl)acetylene and 432 mg. of microcrystalline cellulose.

EXAMPLE 27

Cocoa butter (approximately 2:1 grams) is mixed with (4-(2-fluorophenyl)phenyl)acetylene, (approximately 0.1 gram) and the resulting mixture is melted with gentle heat and poured into a rectal suppository mold of suitable size.

EXAMPLE 28

A tincture suitable for topical administration is prepared with the following ingredients:
(4-(2-fluorophenyl)phenyl) acetylene: 1% by weight
ethanol: 50% by volume
propylene glycol: 20% by volume
water: q.s.100% by volume.

The tincture is prepared by dissolving the (4-(2-fluorophenyl)phenyl)acetylene with the ethanol, and thereafter adding the propylene glycol and water to the final volume.

EXAMPLES 29-52

The compounds of the present invention were evaluated for anti-inflammatory activity by the ultraviolet-induced erythema blocking test. The test procedures were a modification of the Winder method (Winder, C. V.; Wax, J.; Burr, V.; Been, M.; and Posiere, C. E.: A Study of Pharmacological Influences on Ultraviolet Erythema in Guinea Pigs. *Arch. Int. Pharmacodyn.* 116: 261, 1958). Male albino guinea pigs weighing 240-300 gm. were used. The hair on the back was clipped and chemically depilated 15-18 hours before each experiment. The animals were fasted overnight, and on the day of the experiment, were randomized and placed in clear plastic partitioned holders 10×20 cm. wide and 15 cm. high.

The compounds to be tested were suspended in 1% methyl cellulose in water, utilizing a tissue homogenizer. The suspensions were administered orally in a volume of 2.0 ml./kg. of body weight. Control animals received an equal amount of the vehicle.

The source of ultraviolet light was a Hanovia lamp (Kromayer-Model 10). A notebook reinforcement ring was placed upon the lens of the lamp to provide an area of contrast for grading purposes. The lens was then placed in contact with the skin of the guinea pig's back. Exposure time to UV was for a period of 4 seconds. Beginning one hour after exposure and thereafter at half-hour intervals for another 1½ hours, the degree of resulting erythema was graded by an arbitrary scoring system based upon the degree of contrast and redness formed. Anti-inflammatory agents delay the development of the erythema and have their greatest effect at the initial grading periods. The scores were, therefore, weighted by factors of 4, 3, 2, and 1 at the 1.0, 1.5, 2.0, and 2.5 hour scoring times, respectively. The erythema was graded as follows:

| Score | Erythema Scoring System<br>Appearance of Exposed Area |
|---|---|
| 0 | No redness and no contrast |
| 1 | Slight redness with a faint reinforcement outline |
| 2 | Slight to moderate redness with a distinct outline |
| 3 | Marked redness with a distinct circular outline |

Total scores from each treatment group of four guinea pigs were compared to the scores of the control group. The percent inhibition was calculated as follows:

$$100 \times \frac{\text{Control} - \text{Treatment}}{\text{Control}} = \text{Percent Inhibition}$$

In the case of compounds showing inhibition, retesting was carried out at a plurality of doses to enable calculation of an $ED_{50}$ for each such compound. "$ED_{50}$" designates that dose which provides 50% inhibition. Calculation of the $ED_{50}$ was either by a standard linear regression method or by estimation from a dose-response curve of three or more points. The compounds so tested and their $ED_{50}$s were as follows:

| Compound | $ED_{50}$ in mg./kg. |
|---|---|
| 4-biphenylylacetylene | 0.9 |
| 3-biphenylylacetylene | 7 |
| (4-(2-fluorophenyl)phenyl)acetylene | 0.05 |
| (4-(3-fluorophenyl)phenyl)acetylene | 3 |
| (4-(2-chlorophenyl)phenyl)acetylene | 0.8 |
| (4-(2,4-difluorophenyl)phenyl)acetylene | 4 |
| (4-(2,5-difluorophenyl)phenyl)acetylene | 4.4 |
| (2-methoxy-4-phenylphenyl)acetylene | 39 |
| (2-methyl-4-n-butoxyphenyl)acetylene | 35 |
| (3-chloro-4-cyclohexylphenyl)acetylene | 1.0 |
| (3-phenoxyphenyl)acetylene | 13 |
| (2-methyl-4-phenoxyphenyl)acetylene | 8 |
| (3-methyl-4-phenoxyphenyl)acetylene | 10 |
| (3,5-dimethyl-4-phenoxyphenyl)acetylene | 11 |
| (4-(2-fluorophenoxy)phenyl)acetylene | 16.5 |
| (3-(2-fluorophenoxy)phenyl)acetylene | 12 |
| (4-(o-tolyl)phenyl)acetylene | 0.9 |
| (4-(2,6-difluorophenyl)phenyl)acetylene | 12.0 |
| (2-methyl-4-phenylphenyl)acetylene | 0.0 |
| (3-chloro-4-phenylphenyl)acetylene | 0.033 |
| (3-fluoro-4-phenylphenyl)acetylene | 0.5 |
| (4-fluoro-3-(2-fluorophenyl)phenyl)acetylene | 23 |
| (3-methyl-4-phenylphenyl)acetylene | 0.09 |
| (3-methoxy-4-phenylphenyl)acetylene | 0.6 |

EXAMPLE 53

(4-(2-Fluorophenyl)phenyl)acetylene was also evaluated for anti-inflammatory effect when applied topically. The test procedures were the same as those reported in Examples 29-52 except for three differences: the compound was applied topically in an alcohol solution immediately after exposure to the ultraviolet; scores were not weighted; and results were recorded only as percent inhibition. The results were as follows:

| | Erythemic Scores<br>Time after U.V. Exposure | | | | | |
|---|---|---|---|---|---|---|
| Total<br>Amount<br>Applied | 1<br>Hr. | 1.5<br>Hr. | 2<br>Hr. | 2.5<br>Hr. | Total<br>Score | %<br>Inhibition |
| Control<br>(alcohol solution) | 17 | 20 | 20 | 21 | 78 | — |
| 100 µg | 0 | 1 | 4 | 8 | 13 | 83 |
| 10 µg | 5 | 10 | 14 | 17 | 46 | 41 |
| 1 µg | 6 | 13 | 18 | 19 | 56 | 28 |

EXAMPLE 54

(4-(2-Fluorophenyl)phenyl)acetylene was evaluated again by the procedures of Examples 29-52, except that the compound was administered 8 or 22 hours prior to exposure to ultraviolet light. The dose was uniformly 0.5 mg./kg. Readings were made at half-hour intervals beginning at one-half hour after exposure and ending at three and one-half hours after exposure. Scores were not weighted, and results were recorded only as percent inhibition. The results were as reported below.

| Treatment | Scores at Respective Hours after Exposure to Ultraviolet | | | | | | Total Score | % Erythema Inhibition |
|---|---|---|---|---|---|---|---|---|
| | 0.5 | 1.0 | 1.5 | 2.0 | 2.5 | 3.0 | | |
| Control | 8 | 16 | 18 | 20 | 21 | 21 | 104 | — |
| 0.5 mg./kg. of (4-(2-fluorophenyl)phenyl)-acetylene 8 hours prior to ultraviolet exposure | 0 | 0 | 3 | 6 | 6 | 15 | 30 | 71 |
| Control | 7 | 18 | 19 | 21 | 21 | 21 | 107 | — |
| 0.5 mg./kg. of (4-(2-fluorophenyl)phenyl)-acetylene 22 hours prior to ultraviolet exposure | 3 | 4 | 8 | 14 | 17 | 17 | 63 | 41 |

EXAMPLE 55

(4-(2-Fluorophenyl)phenyl)acetylene was also evaluated for the control of inflammation in dogs. The testing procedures were the same as reported in the preceding examples except for these differences: a 10-second exposure time was used; non-pigmented abdominal skin was used; and the observed erythema was graded every half hour over a three-hour period with no weighting of scores. A placebo control was run with the same test dogs on the day prior to treatment. The results were as follows:

| Dog No. | Dose | Total Erythemic Score | % Erythema Inhibition |
|---|---|---|---|
| 05 | Control | 14 | — |
| 05 | 10 mg/kg | 0 | 100 |
| 04 | Control | 15 | — |
| 04 | 5 mg/kg | 0 | 100 |
| 05 | Control | 14 | — |
| 05 | 1 mg/kg | 4 | 71 |

EXAMPLES 56-58

Representative compounds of the present invention were evaluated for anti-inflammatory activity in rats using an adjuvant-induced arthritis test.

The test method was that of Winter et al., 9 *Arthritis and Rheumatism* 394 (1966). Male, specific pathogen-free albino rats, weighing approximately 200 g., were used. The arthritic syndrome was induced by injection of 0.05 ml. of a fine suspension of dead *Mycobacterium tuberculosum* bacilli in mineral oil (concentration 5mg./ml.) through a needle into the plantar surface of the right hind foot. The tubercle bacilli were derived from human strains PN, DT and C which were grown for eight weeks, killed by steam and dried in a vacuum oven.

One day before injection of adjuvant and daily thereafter for thirteen days, a suspension of test compound in 1% sodium carboxymethylcellulose in water was administered orally to rats. In control rats an edematous paw was induced which reached its maxium size between about day 7 and day 10.

A measurement of the edema of the tested rats was made by dipping the rat's foot into a well, displacing mercury. The pressure from the mercury was transferred into electrical output by a Digital Volumetric Measurement System, using a transducer. The paw volume was measured on the day adjuvant was administered (day two) and again on day seven and day fourteen of the test. The initial (day two) volume was subtracted from the volumes on the seventh and on the fourteenth days, and the percent volume increases were calculated. Percent inhibition was calculated by comparing percent increases of treated and control groups. All readings and measurements were done in blind studies. The activities of the compounds measured by this test are shown below.

| Compound | Dose | Percent Inhibition of Volume Increase | |
|---|---|---|---|
| | | Day 7 | Day 14 |
| 4-biphenylylacetylene | 25 | 29 | 37 |
| | | 37 | 23 |
| | 3 | 14 | 7 |
| | 1 | 0 | 0 |
| | 0.3 | 15 | 0 |
| (2-(2,5-difluorophenyl)phenyl)-acetylene | 25 | 38 | 15 |
| (3-chloro-4-phenylphenyl)acetylene | 3 | 30 | 45 |
| | 1 | 34 | 41 |
| | 0.3 | 56 | 50 |
| | 0.1 | 21 | 36 |

EXAMPLE 59

(4-(2-Fluorophenyl)phenyl)acetylene was evaluated repeatedly by the procedures reported in Examples 56-58. In two sets of representative tests, the compounds performed as reported in the following table:

| Dose | Percent Inhibiton of Volume Increase | |
|---|---|---|
| | Day 7 | Day 14 |
| 10 | 30 | 5 |
| 3 | 35 | 21 |
| 1 | 27 | 14 |
| 10 | 23 | 0 |
| 3 | 29 | 0 |
| 1 | 22 | 0 |

EXAMPLES 60-80

Representative compounds were also evaluated for anti-inflammatory activity in the test method described by C. A. Winter at 111 *Proc. Soc. Exp. Biol. Med.*, 544 (1962). In this method, inflammation is created by injecting carrageenin into the hind paw of rats. Test compounds are administered prior to injection to determine percent inhibition of the subsequent inflammation, in comparison with control animals. The results were as reported below.

| Compound | Dose in mg./kg. | % inhibition |
|---|---|---|
| (2-methyl-4-phenoxyphenyl)acetylene | 25 | 33 |
| (3-phenoxyphenyl)acetylene | 10 | 7 |
| (3-methyl-4-phenoxyphenyl)acetylene | 10 | 16 |
| (3,5-dimethyl-4-phenoxyphenyl)acetylene | 50 | 29 |
| 4-biphenylylacetylene | 50 | 41 |
|  | 20 | 45 |
|  | 10 | 42 |
|  | 5 | 37 |
|  | 10 | 56 |
|  | 3 | 36 |
|  | 1 | 0 |
|  | 5 | 26 |
|  | 1 | 0 |
|  | 0.5 | 0 |
|  | 10 | 51 |
|  | 3 | 41 |
|  | 1 | 45 |
| (4-(3-fluorophenyl)phenyl)acetylene | 10 | 17 |
| (4-(2,4-difluorophenyl)phenyl)acetylene | 25 | 31 |
| (4-(2,5-diflurophenyl)phenyl)acetylene | 25 | 43 |
| (2-methoxy-4-phenylphenyl)acetylene | 50 | 51 |
|  | 10 | 7 |
|  | 1 | 25 |
| (2-methyl-4-n-butoxyphenyl)acetylene | 25 | 9 |
| (4-(2-fluorophenyl)phenyl)acetylene | 25 | 65 |
|  | 10 | 51 |
|  | 2.5 | 35 |
|  | 1 | 29 |
|  | 3 | 57 |
|  | 1 | 31 |
|  | 0.3 | 21 |
|  | 50 | 57 |
|  | 15 | 56 |
|  | 5 | 43 |
|  | 10 | 52 |
|  | 3 | 35 |
|  | 1 | 43 |
|  | 5 | 36 |
|  | 1.5 | 29 |
|  | 0.5 | 6 |
|  | 10 | 30 |
|  | 3 | 32 |
|  | 1 | 0 |
|  | 5 | 35 |
|  | 1 | 29 |
|  | 0.5 | 6 |
| (4-(2-chlorophenyl)phenyl)acetylene | 50 | 52 |
| 3-biphenylylacetylene | 50 | 32 |
| (3-chloro-4-phenylphenyl)acetylene | 10 | 62 |
|  | 3 | 41 |
|  | 0.3 | 23 |
| (3-methyl-4-phenylphenyl)acetylene | 50 | 66 |
|  | 30 | 56 |
|  | 10 | 56 |
|  | 3 | 37 |
| (4-(o-tolyl)phenyl)acetylene | 50 | 48 |
|  | 30 | 53 |
|  | 10 | 6 |
|  | 3 | 16 |
| (3-(2-fluorophenoxy)phenyl)acetylene | 50 | 32 |
| (4-(2-fluorophenoxy)phenyl)acetylene | 30 | 68 |
|  | 10 | 45 |
|  | 10 | 44 |
|  | 3 | 28 |
| (4-fluoro-3-(2-fluorophenyl)phenyl)acetylene | 50 | 45 |
|  | 30 | 43 |
|  | 10/ 23 |  |
|  | 3 | 13 |
| (4-(2,6-difluorophenyl)phenyl)acetylene | 50 | 49 |
|  | 30 | 37 |
|  | 10 | 34 |
|  | 3 | 7 |
| (3-fluoro-4-phenylphenyl)acetylene | 50 | 54 |
|  | 50 | 77 |

EXAMPLES 81-82

Each of 4-biphenylylacetylene and (4-(2-fluorophenyl)phenyl)acetylene was evaluated again in the carrageenin induced test method reported in Examples 60-80. However, in these tests, the compound was administered about 20 hours prior to the test procedures. The results were as follows:

|  | Dose | % Inhibitin |
|---|---|---|
| 4-biphenylylacetylene | 10 | 44 |
|  | 10 | 28 |
| (4-(2-fluorophenyl)phenyl)acetylene | 10 | 42 |
|  | 10 | 60 |

EXAMPLE 83

(4-(2-Fluorophenyl)phenyl)acetylene was evaluated for antipyretic effect in rats. Fever was induced by subcutaneous injection of yeast, a technique reported at 54 J. Pharm. Exp. Ther. 346 (1935). A total of 24 rats was employed, divided into 6 treatment groups. One group was a normal control, without even the yeast injection. A second group served as a yeast control, receiving yeast injection but none of the test compound. All of the remaining groups received the test compound, in the following pattern:
  no yeast+100 mg./kg. of compound
  yeast+100 mg./kg. of compound
  yeast+50 mg./kg. of compound
  yeast+10 mg./kg. of compound The procedure was that yeast was administered to all rats at the same time and temperatures were ascertained two hours later, at which time the test compound was administered to those groups assigned to receive it. Temperatures of all animals were also recorded thereafter at 1.0, 1.5, 2.0, 2.5, and 3.0 hours following administration of the test compound.

Resulting data was analyzed statistically, showing the following:

(1) Comparing all rats receiving yeast with all rats not receiving yeast, the former exhibited mean temperatures above the mean temperatures of the latter, and the differences were statistically significant. This confirms the validity of the fever-inducing technique.

(2) In rats receiving no yeast injection, some lowering of temperature occurred after administration of (4-(2-fluorophenyl)phenyl)acetylene, but the change was not statistically significant when compared with differences observed in the normal control and yeast control groups.

(3) Temperatures of all rats receiving both yeast and (4-(2-fluorophenyl)phenyl)acetylene were uniformly lower following administration of the test compound for all three dose levels of (4-(2-fluorophenyl)phenyl-)acetylene and at all reading times. At the 1.5 hour reading for each of 50 mg./kg. and 100 mg./kg. and at the 1.0 hour reading for all dose levels, the differences were not statistically significant. At all other doses, the differences were statistically significant, indicating that (4-(2-fluorophenyl)phenyl)acetylene exhibited antipyretic action.

EXAMPLES 84–102

Representative compounds were also evaluated for analgesic activity. The evaluation was conducted by using acetic acid-induced writhing in mice as the pain model. Clinically effective analgesis are effective when tested in this model: see Koster et al., "Acetic Acid for Analgesic Screening," 18 Fed. Proc. 412 (1959).

In a method similar to that reported by Koster et al., standard strain albino male mice weighing 20–22 grams were fasted overnight. The respective compound or vehicle (as control) was administered by gastric lavage (p.o.). Each compound was administered in an aqueous suspension of 1% methylcellulose in water. Control mice received comparable amounts of the vehicle only. At 30, 90, and 180 minutes after administration, writhing was induced by the intraperitoneal administration of 55 mg./kg. of acetic acid (0.55%). Each treatment group consisted of 5 mice and separate groups were examined at each observation time. The total number of writhes for the treatment group were counted in a 10-minute observation period starting 5 minutes after the acetic acid administration. The treatment totals were compared to controls and a percent inhibition calculated as follows:

$$\% \text{ Inhibition} = 100 - \frac{\text{Treatment total}}{\text{Control total}} \times 100$$

If a compound inhibited writhing at 100 mg./kg., lower doses were generally examined. An ED$_{50}$, which represented the dose that would reduce the writhing frequency by 50%, was estimated from a dose-response curve of three or more points. A dose range was reported if only two points were available for the dose response curve and they bracketed the 50% level. If data was available at 100 mg./kg. only, then the estimated ED$_{50}$ was reported simply as less than 100 (<100).

The results were as reported below:

| Compound | Estimated ED$_{50}$, mg./kg. |
| --- | --- |
| 4-biphenylylacetylene | 50 |
| 3-biphenylylacetylene | 50–100 |
| (4-(o-tolyl)phenyl)acetylene | 35 |
| (2-methyl-4-phenylphenyl)acetylene | 60 |
| (3-methyl-4-phenylphenyl)acetylene | 50 |
| (4-(2-chlorophenyl)phenyl)acetylene | 20–100 |
| (3-chloro-4-cyclohexylphenyl)acetylene | <100 |
| (3-chloro-4-phenylphenyl)acetylene | 30 |
| (4-(2-fluorophenyl)phenyl)acetylene | 20 |

| Compound | Estimated ED$_{50}$, mg./kg. |
| --- | --- |
| (4-(3-fluorophenyl)phenyl)acetylene | 35 |
| (4-(2,4-difluorophenyl)phenyl)acetylene | 4 |
| (4-(2,5-difluorophenyl)phenyl)acetylene | 10 |
| (4-(2,6-difluorophenyl)phenyl)acetylene | <100 |
| (3-fluoro-4-phenylphenyl)acetylene | 10 |
| (4-(2-fluorophenoxy)phenyl)acetylene | <100 |
| (3-phenoxyphenyl)acetylene | <100 |
| (2-methyl-4-phenoxyphenyl)acetylene | <100 |
| (3-methyl-4-phenoxyphenyl)acetylene | <100 |
| (3,5-dimethyl-4-phenxyphenyl)acetylene | <100 |

The compounds to be employed as starting materials in the

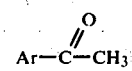

first synthetic route: are themselves prepared in known procedures. Several such procedures are as follows:

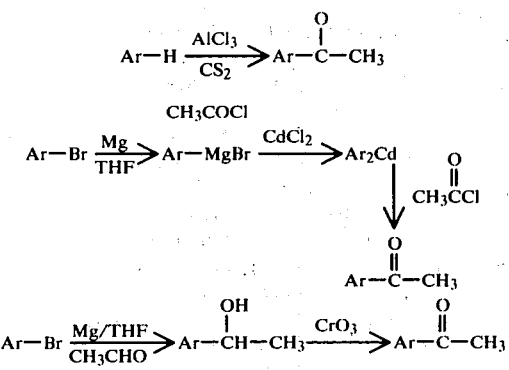

Similarly, the compounds to be employed as the starting materials in the second synthetic route are also prepared in known procedures:

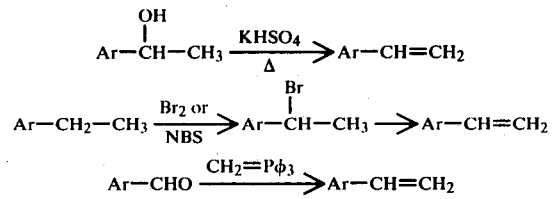

Representative preparations follow.

A solution of 200 g. of 2-fluorobiphenyl in 1500 ml. of CS$_2$ was cooled to 0°–5° C. and treated with 200 g. of aluminum chloride over 140 minutes and then with 113 g. of acetyl chloride over 165 minutes. The mixture was allowed to warm to room temperature and stirred overnight. The reaction mixture was then poured carefully into ice and hydrochloric acid, and organic material was extracted with a mixture of diethyl ether and ethyl acetate. The organic extract was washed with water, 10% sodium hydroxide, and water, and dried over sodium sulfate. Evaporation of the solvents in vacuo and recrystallization of the solid residue from hexane gave (4'-(2-fluorophenyl)acetophenone. This was recrystallized from hexane to give two crops.

Crop one, 173 g., m.p. 84.5°–86.5° C.

Analysis, Calc. for $C_{14}H_{11}FO$: C, 78.49; H, 5.18; F, 8.87. Found: C, 77.23; H, 4.75; F, 10.00.

Crop two, 51.1g., m.p. 85°–87° C.

Analysis, Calc. for $C_{14}H_{11}FO$: C, 78.49; H, 5.18; F, 8.87.

Found: C, 78.40; H, 5.35; F, 8.89.

In another preparation, a Grignard reagent was prepared from 100 g. of 3-bromobiphenyl and 10 g. of Mg in diethyl ether. To this solution was added 40 g. of $CdCl_2 \cdot 2H_2O$ at 4° C. during one hour. The reaction mixture was then refluxed for an hour, cooled, and a diethyl ether solution of 32 g. of acetyl chloride added at 12° C. over a period of 30 minutes. The reaction mixture was refluxed for 30 minutes and allowed to cool at room temperature and stir overnight. Additional diethyl ether was added and the reaction mixture was refluxed for an hour. After cooling, 100 ml. of ammonium chloride solution was added, followed by 100 ml. of water. The reaction mixture was poured onto ice and the diethyl ether layer separated. The diethyl ether extract was washed with water (until the washes were neutral), dried over sodium sulfate, and evaporated to dryness. The residue was distilled to yield 29.3 g. of 3'-phenylacetophenone, b.p. 120° C./0.3 mm., after low boiling earlier fractions had been separated.

Analysis, Calc. for $C_{14}H_{12}O$: C, 85.68; H, 6.16; O, 8.15. Found: C, 85.62; H, 6.33; O, 8.18.

In another preparation, a Grignard reagent was prepared by allowing 5.3 g. of Mg to react with 54 g. of 2-fluoro-4-bromobiphenyl in tetrahydrofuran. A solution of 9.7 g. of acetaldehyde in 100 ml. of tetrahydrofuran was added dropwise to the cooled Grignard solution. After addition was complete another 125 ml. of tetrahydrofuran was added and the solution was stirred overnight at room temperature.

After cooling, 165 ml. of saturated ammonium chloride solution were added dropwise followed by 100 ml. of water. After warming to room temperature, the reaction mixture was poured onto ice. The product was extracted into ether and the ether extract was washed three times with water, dried over sodium sulfate, and the ether was evaporated in vacuo. The solid residue was crystallized from hexane to yield 26.3 g. of α-methyl-3-fluoro-4-phenylbenzyl alcohol, m.p. 84°–86° C.

Analysis, Calc. for $C_{14}H_{13}FO$: C, 77.76; H, 6.06 Found: C, 77.52; H, 6.33.

A solution of 12 g. of $CrO_3$ in 42 ml. of 35% sulfuric acid was added dropwise to a well stirred, cooled solution of 28.6 g. of α-methyl-3-chloro-4-phenylbenzyl alcohol in 36 ml. of acetone. A large volume of additional acetone was then added and the aqueous layer separated. This was separated and washed with additional acetone, and the combined acetone solutions were dried over sodium sulfate and evaporated. The residual liquid was distilled to yield 26.3 g. of 3'-chloro-4'-phenylacetophenone b.p. 132°–141° C./0.09 mm.

Analysis, Calc. for $C_{14}H_{11}ClO$: C, 72.89; H, 4.81. Found: C, 72.63; H, 4.85.

We claim:

1. A method of treating inflammation, fever, or pain in a warm-blooded animal which comprises administering to the animal an effective amount of an active agent which is 4-biphenylyacetylene.

2. A method of treating inflammation in a warm-blooded animal which comprises administering to the animal an effective amount of an active agent which is 4-biphenylylacetylene.

3. A pharmaceutical preparation in dosage unit form adapted for administration to obtain an anti-inflammatory, anti-pyretic, or analgesic effect, comprising, per dosage unit, an effective non-toxic amount within the range from about 1 to about 1000 milligrams of an active agent, and a pharmaceutical diluent, said active agent being 4-biphenylacetylene.

* * * * *